(12) United States Patent
Woo et al.

(10) Patent No.: US 11,141,507 B2
(45) Date of Patent: Oct. 12, 2021

(54) MAGNESIUM-BASED SUTURE ANCHOR DEVICES

(71) Applicant: UNIVERSITY OF PITTSBURGH—OF THE COMMONWEALTH SYSTEM OF HIGHER EDUCATION, Pittsburgh, PA (US)

(72) Inventors: Savio L-Y. Woo, Pittsburgh, PA (US); Kwang E. Kim, Pittsburgh, PA (US); Jonquil R. Flowers, Pittsburgh, PA (US)

(73) Assignee: University of Pittsburgh—Of The Commonwealth System of Higher Education, Pittsburgh, PA (US)

(*) Notice: Subject to any disclaimer, the term of this patent is extended or adjusted under 35 U.S.C. 154(b) by 553 days.

(21) Appl. No.: 15/561,861

(22) PCT Filed: Nov. 6, 2015

(86) PCT No.: PCT/US2015/059591
§ 371 (c)(1),
(2) Date: Sep. 26, 2017

(87) PCT Pub. No.: WO2016/073933
PCT Pub. Date: May 12, 2016

(65) Prior Publication Data
US 2018/0110904 A1     Apr. 26, 2018

Related U.S. Application Data

(60) Provisional application No. 62/077,199, filed on Nov. 8, 2014.

(51) Int. Cl.
*A61L 31/02*      (2006.01)
*A61L 31/14*      (2006.01)
(Continued)

(52) U.S. Cl.
CPC ........ *A61L 31/022* (2013.01); *A61B 17/0401* (2013.01); *A61L 31/148* (2013.01);
(Continued)

(58) Field of Classification Search
CPC ...... A61B 2017/044; A61B 2017/0459; A61B 17/86; A61B 17/8605; A61B 17/861;
(Continued)

(56) References Cited

U.S. PATENT DOCUMENTS

| 4,312,336 A * | 1/1982 | Danieletto ............. A61B 17/66 606/57 |
| 2008/0109038 A1 | 5/2008 | Steiner et al. |

(Continued)

OTHER PUBLICATIONS

Form PCT/ISA/220, PCT Notification of Transmittal of the International Search Report and the Written Opinion of the International Searching Authority, or the Declaration, PCT/US2015/059591, dated Jan. 29, 2016.
(Continued)

*Primary Examiner* — Thomas McEvoy
(74) *Attorney, Agent, or Firm* — Paul D Bangor, Jr., Esquire; Clark Hill PLC

(57) ABSTRACT

A suture anchor apparatus comprising: an anchoring member made from a metal-based material and comprising a generally elongated body having a proximal end and a distal end, wherein an outer surface of the anchoring member defines a threading that winds around the body in a plurality of turns disposed along a longitudinal axis of the body; wherein the threading has a depth of about 1 mm and a pitch of about 3 mm, and an eyelet disposed near the distal end and penetrating transversely through the body.

19 Claims, 1 Drawing Sheet

(51) Int. Cl.
*A61B 17/04* (2006.01)
*A61L 31/18* (2006.01)
*A61B 17/00* (2006.01)

(52) U.S. Cl.
CPC ..... *A61L 31/18* (2013.01); *A61B 2017/00004* (2013.01); *A61B 2017/00893* (2013.01); *A61B 2017/00911* (2013.01); *A61B 2017/044* (2013.01); *A61B 2017/0414* (2013.01); *A61L 2430/02* (2013.01)

(58) Field of Classification Search
CPC .............. A61B 17/8615; A61B 17/862; A61B 17/8625; A61B 17/863; A61B 17/8635; A61B 17/864; A61B 17/8645; A61B 17/8655
See application file for complete search history.

(56) References Cited

U.S. PATENT DOCUMENTS

| | | |
|---|---|---|
| 2009/0081313 A1 | 3/2009 | Aghion et al. |
| 2011/0313527 A1 | 12/2011 | Witte et al. |
| 2012/0143227 A1 | 6/2012 | Steckel et al. |
| 2013/0253581 A1* | 9/2013 | Robison ............ A61B 17/0401 606/232 |
| 2014/0243911 A1* | 8/2014 | Almarza ............ A61B 17/8605 606/305 |

OTHER PUBLICATIONS

Form PCT/ISA/210, PCT International Search Report for International Application No. PCT/US2015/059591, dated Jan. 29, 2016.
Form PCT/ISA/237, PCT Written Opinion of the International Searching Authority for International Application No. PCT/US2015/059591, dated Jan. 29, 2016.
Form PCT/IB/326, PCT Notification Concerning Transmittal of International Preliminary Report on Patentability, PCT/US2015/059591, dated May 18, 2017.
Form PCT/IB/373, PCT International Preliminary Report on Patentability for International Application No. PCT/US2015/059591, dated May 18, 2017.
Farraro, Kathryn F., et al, "Revolutionizing Orthopaedic Biomaterials: The Potential of Biodegradable and Bioresorbable Magnesium-based Materials for Functional Tissue Engineering", Journal of Biomechanics, Jun. 27, 2014, vol. 47, No. 9, pp. 1979-1986.

* cited by examiner

Maximum von Mises stress in the finite element model vs. thread depth

MAGNESIUM-BASED SUTURE ANCHOR DEVICES

CROSS REFERENCE TO RELATED APPLICATIONS

This application claims the benefit of the filing date of U.S. provisional patent application Ser. No. 62/077,199, filed on Nov. 8, 2014, the entirety of which is incorporated herein by reference for all purposes.

STATEMENT REGARDING FEDERALLY SPONSORED RESEARCH OR DEVELOPMENT

This invention was made with government support under grant #0812348 from the National Science Foundation. The government has certain rights in the invention.

BACKGROUND OF THE DISCLOSURE

As many as 800,000 surgical treatments of musculoskeletal soft tissue injuries are performed each year in the U.S. Suture anchors are used to attach tendon to bone during repair of injured soft tissue for rotator cuff tears, femoral acetabular impingements (FAI), meniscus tears, and Achilles tendon ruptures. For example, as many as 300,000 rotator cuff repair surgeries are performed in the U.S. annually. With the use of 2 to 4 suture anchors for each surgical procedure, suture anchors account for billions of dollars in healthcare costs.

Suture anchors must be able to provide secure soft tissue fixation and resist common suture anchor failures such as breakage, eyelet failure, and pullout. However, typical metallic suture anchors currently available suffer from disadvantages such as migration, loosening, revision surgery difficulties and they interfere with postoperative imaging techniques. Typical polymer suture anchors currently available suffer from disadvantages such as breakage and unpredictable degradation and they are associated with osteolysis.

Thus, it would be desirable to have available suture anchors that eliminate such problems exhibited by designs in soft tissue fixation and that effectively allow for pain relief and overall increased quality of life that result from successful soft tissue fixation procedures, such as rotator cuff repair. Further it would be desirable to have available suture anchors for use in repair of numerous other soft tissues in the musculoskeletal system.

SUMMARY

In a preferred aspect, the present disclosure is directed to a suture anchor apparatus comprising: an anchoring member made from a metal-based material and comprising a generally elongated body having a proximal end and a distal end, wherein an outer surface of the anchoring member defines a threading that winds around the body in a plurality of turns disposed along a longitudinal axis of the body; wherein the threading has a depth of about 1 mm and a pitch of about 3 mm, and an eyelet disposed near the distal end and penetrating transversely through the body.

In another preferred aspect, the metal-based material comprises magnesium or a magnesium alloy. In a further preferred aspect, the metal-based material comprises an AZ31 magnesium alloy.

In another preferred aspect, the metal-based material causes no interference with the operation of an MRI device. In yet another preferred aspect, the metal-based material is biodegradable.

In another preferred aspect, the metal-based material is biodegradable and causes no interference with the operation of an MRI device.

In still a further preferred aspect, the metal-based material has a rate of biodegradability that is uniform over time.

In another preferred aspect, the metal-based material has a rate of biodegradability that has been customized by the inclusion of alloying materials selected from the group consisting of calcium, zinc and manganese, and/or by surface treatments.

In yet another preferred aspect, the metal-based material promotes bone growth, or has high osteoinductivity or high osteointegration.

In another preferred aspect, the rate of biodegradability corresponds to an anticipated healing time.

In a further preferred aspect, the rate of biodegradability corresponds to an anticipated healing time such that the anchoring member will only completely degrade after such anticipated healing time has passed.

In another preferred aspect, the metal-based material comprises a magnesium alloy and is biodegradable.

In yet another preferred aspect, the metal-based material comprises a magnesium alloy and is biodegradable and causes no interference with the operation of an MRI device.

In still another preferred aspect, the metal-based material comprises a magnesium alloy and has a rate of biodegradability that is uniform over time.

In another preferred aspect, the metal-based material comprises a magnesium alloy and has a rate of biodegradability that has been customized by the inclusion of alloying materials selected from the group consisting of calcium, zinc and manganese, and/or by surface treatments.

In another preferred aspect, the metal-based material comprises a magnesium alloy and promotes bone growth, or has high osteoinductivity or high osteointegration.

In a further preferred aspect, the metal-based material comprises a magnesium alloy and the rate of biodegradability corresponds to an anticipated healing time.

In another preferred aspect, the metal-based material comprises a magnesium alloy and the rate of biodegradability corresponds to an anticipated healing time such that the anchoring member will only completely degrade after such anticipated healing time has passed.

In still a further preferred aspect, the metal-based material comprises a magnesium alloy and the metal-based material has a rate of biodegradability that has been customized by the inclusion of alloying materials and/or by surface treatments.

DETAILED DESCRIPTION

Figure 1:
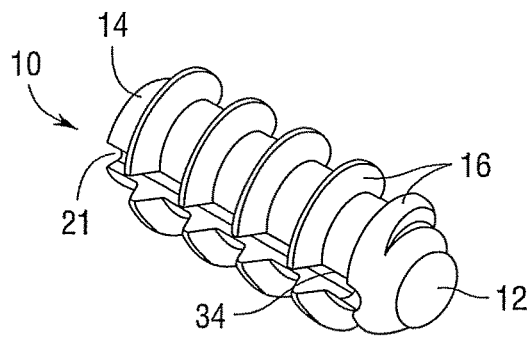
FIG. 1 shows a perspective view of a suture anchor according to a preferred embodiment of the present disclosure.
Figure 2:
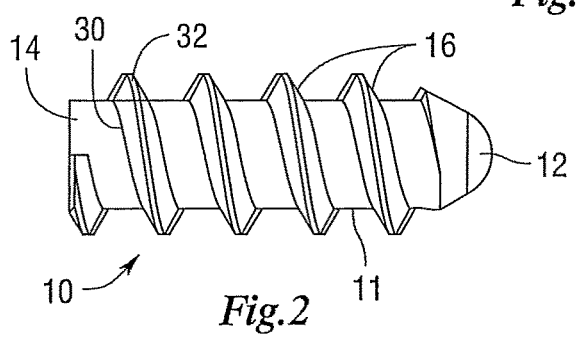
FIG. 2 shows a side view of the suture anchor of FIG. 1.
Figure 3:
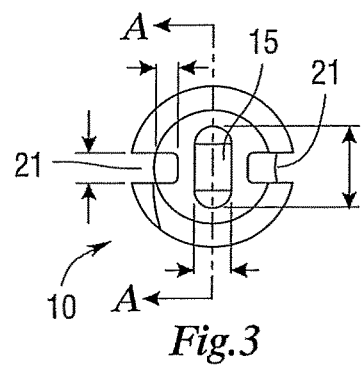
FIG. 3 shows an end view of the suture anchor of FIG. 1.
Figure 4:
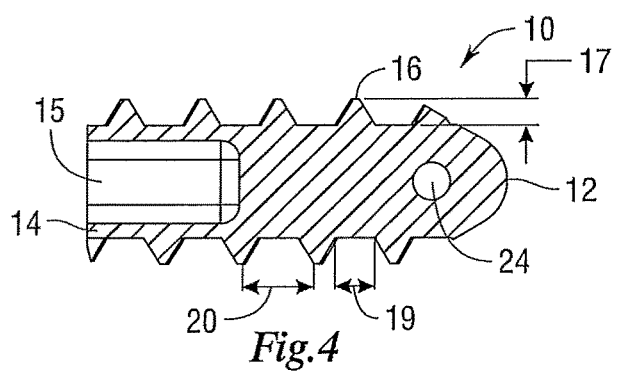
FIG. 4 is a cross-sectional view of the suture anchor of FIG. 1 along line A-A of FIG. 3.

It is to be understood that the descriptions of the present disclosure have been simplified to illustrate elements that are relevant for a clear understanding of the present disclosure, while eliminating, for purposes of clarity, other elements that may be well known. Those of ordinary skill in the art will recognize that other elements are desirable and/or required in order to implement the present disclosure. However, because such elements are well known in the art, and because they do not facilitate a better understanding of the present disclosure, a discussion of such elements is not provided herein. Additionally, it is to be understood that the present disclosure is not limited to the embodiments described above, but encompasses any and all embodiments within the scope of the description and the following claims.

FIGS. 1-4 show a preferred embodiment of suture anchor 10 of the present disclosure comprising an elongate implant body 11, nose or endpoint 12. The implant body extends from a proximal end 14 to a distal end at nose 12 along a longitudinal axis (not shown). Nose 12 tapers distally to ease insertion of the anchor 12 during implantation into bone. An axial passage 15 preferably extends into the body 11 proximally to distally about 6 mm into proximate end 14 along the longitudinal axis. Preferably, axial passage 15 may be of any required size and shape for receiving an insertion device used for implanting anchor 10. Transverse aperture 24 extends through the body 11 preferably near its distal end near nose 12. Preferably, the body 12 has radially extending threads or ridges 16 that taper from a wider base 30 to a narrower outer most edge 32. Preferably, threads 16 have a height 17 of about 1 mm. The bases 30 have a preferred spacing 19 of about 1-2 mm and most preferably of about 1.6 mm. Edges 32 have a preferred spacing 20 of about 2-3 mm and most preferably of about 2.8 mm. Threads 16 aid in retaining the body 11 in bone after implantation. Opposed flats 34 extend along opposite sides of the body 11 within slots 21 and intersect with aperture 24 to provide clearance for suture ends extending alongside the body 11. One or more suture strands to be anchored by anchor 10 may be passed through the aperture 24.

Preferably, suture anchor 10 of the present disclosure is made of a magnesium alloy, such as AZ31. Further, suture anchor 10 of the present disclosure preferably may be made from any magnesium allowing for use in repair of rotator cuff tears, femoral acetabular impingements (FAI), meniscus tears, and Achilles tendon ruptures and/or numerous other soft tissues in the musculoskeletal system. The preferred Mg-based suture anchors 10 of the present disclosure take advantage of high-performance biodegradable Mg alloys to eliminate many problems of soft tissue fixation and effectively allows for pain relief and overall increased quality of life that result from successful soft tissue repair. The Mg-based suture anchors 10 of the present disclosure will shift the clinical paradigm for management of soft tissue injuries.

Mg-based suture anchors 10 of the present disclosure provide the following advantages in the fixation of soft tissues to bone in orthopedic surgery:

1. Superior Fixation—Mg-based suture anchors 10 of the present disclosure provide superior fixation over commercially available bioresorbable polymer suture anchors because of their superior mechanical properties (high ductility and tensile strength) compared to polymer-based materials;

2. Superior Stiffness and Pull-Out Resistance-tensile testing of the Mg-based suture anchors 10 of the present disclosure showed that they provide superior stiffness and require significantly higher pull-out force compared to polymer suture anchors;

3. Superior Strength—the Mg-based suture anchors 10 of the present disclosure have higher tensile strength and ductility and thus are advantageous as new sutures and suturing techniques are being introduced in soft tissue repair which lead to higher mechanical strength demands on suture anchors that currently available biodegradable polymers do possess to meet such demands;

4. Improved Biodegradability—the Mg-based suture anchors 10 of the present disclosure have been determined to be a superior class of biodegradable material over biodegradable polymers for fixation of a soft tissue to bone as they possess the following traits: (i) controlled-degradation: Mg-based suture anchor 10 are amenable to alloying and surface treatments that can effectively control the degradation rate (and even can be customized and made to degrade at a desired rate so that it can be tailored for the required degradation rate for a particular healing protocol where suture anchor 10 gradually disappears and allows the healing tissue to take over the function application, e.g., as the healing rate of different soft tissues differ greatly, this is a great advantage over polymer-based bioresorbable suture anchors) while polymer-based materials are known to exhibit unpredictable degradation rates; and (ii) osteoinductivity: Mg-based suture anchors 10 have been shown to promote bone regeneration leading to good healing of the reattached soft tissue to bone while polymer-based materials have been known to possess poor osteointegration;

No MRI interference: the Mg-based suture anchors 10 of the present disclosure do not cause MRI interference, while traditional metallic materials (such as titanium-based alloys) have significant artifacts on MRI images, making them impossible to interpret.

A 3D model of the Mg-based suture anchor 10 of the present disclosure was subjected to tensile testing in a finite element analysis software to test its performance. At 400 N load (pull-out strength of polymer suture anchors from literature), stresses (130 MPa) in the suture anchor 10 is well below the strength a Mg-based alloy AZ31 (260 MPa) used for making suture anchors 10. Stress distribution in the suture anchor 10 with 400 N applied to the suture eyelet 24 showed that maximum stress was located at the thread 16 adjacent to the eyelet 24. The maximum value was 130 MPa well below the strength of AZ31 material of the suture anchor 10

Figure 5:
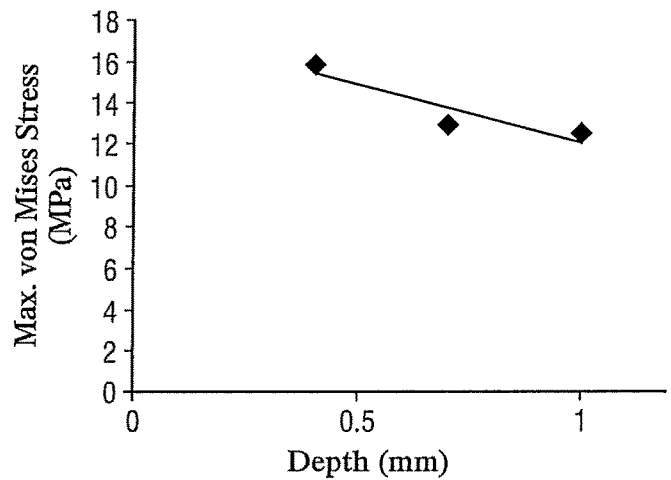
FIG. 5. shows maximum von Mises stress in the finite element model of an Mg-based suture anchor according to a preferred embodiment of the present disclosure vs. thread depth.

The increased thread depth in the Mg-based suture anchors 10 of the present disclosure provided for reduced stress in the surrounding bone where failure occurs (see FIG. 5). Preferably, the Mg-based suture anchors 10 of the present disclosure have 1 mm thread depth and 3 mm thread pitch. The thread design of the Mg-based suture anchors 10 of the present disclosure could be made better than those of polymer suture anchors, i.e., the threads 16 could be deeper because of superior mechanical properties of the Mg-based materials used to make the suture anchors 10. Computational analysis using a finite element analysis software showed that this improved fixation of the Mg-based suture. With polymer materials, this is not possible due to their inferior mechanical properties. With the deeper thread, the number of turns of the thread 16 in the Mg-based suture anchors 10 of the present disclosure could be reduced to make insertion easier during surgery. This was only possible due to the superior mechanical properties of the Mg-based alloys used in suture anchors 10 compared to polymers. Polymer suture anchors require more number of turns of the thread in an effort to provide adequate fixation, which often does not happen with polymer suture anchors.

Preferably, the Mg-based suture anchors 10 of the present disclosure can have tailored degradation rates by adding biocompatible alloying components, calcium, zinc, or manganese.

Application—bioresorbable suture anchors 10 made of Mg-based alloys can be used for any application of fixation of a soft tissue to a bone because they can be made in to any size and degrade at a desired rate. This allows them to be used for applications that require either large or small suture anchors.

The Mg-based suture anchors 10 of the present disclosure have the desirable properties that effectively address the shortfalls of existing metallic and polymeric suture anchors. Mg alloys are a novel class of biodegradable metallic materials that have superior mechanical properties and improved osteointegration compared to polymeric materials while allowing for controlled rates of degradation (eliminating the need for device removal) and minimizing interference in magnetic resonance imaging compared to traditional metallic materials. Also, the osteoinductive property of Mg will enhance bone healing, resulting in improvements in the healing tissue. Thus, the Mg-based suture anchor 10 of the present disclosure will provide secure fixation for rotator cuff repair and other soft tissue repairs with enhance healing, leading to restoration of function with a device that is not permanent.

Biomechanical evaluation of the Mg-based suture anchors 10 of the present disclosure was conducted in the rotator cuff repair in a goat shoulder and provided the following results:
Residual Elongation: 2 mm
Ultimate Load: 200 N
Stiffness: 23 N/mm
Failure mode: Tendon-Suture Interface These results show that the Mg-based suture anchor 10 of the present disclosure is adequate for soft tissue fixation. The Mg-based suture anchor 10 serves to repair a torn tendon to the bone. As a uniaxial load is applied to the repaired tendon-bone construct, the suture anchor 10 remains in the bone, which indicates that the suture anchor 10 functions safely and efficiently and that the weakest link of the repaired construct is the tendon-suture interface.

Mechanical evaluation of the Mg-based suture anchors 10 of the present disclosure was conducted following an industry-standard testing method using a polyurethane foam block of 15 pcf. Compared to a commercially available polymer suture anchor of similar dimensions (6.5 mm diameter by 16.5 mm length), the Mg-based suture anchors 10 of the present disclosure exhibited significantly higher stiffness (80% higher) and significantly higher pull-out strength (100% higher), see Table 1. It was found that polymer suture anchors failed through eyelet failure, whereas the Mg-based suture anchors 10 of the present disclosure remained intact and were pulled out.

TABLE 1

| | Mg-Based Suture Anchor | Polymer Suture Anchor |
|---|---|---|
| Stiffness (N/mm) | 185 ± 13* | 107 ± 13* |
| Pull-out strength (N) | 379 ± 34* | 210 ± 13* |
| Ultimate Elongation (mm) | 2.4 ± 0.2* | 1.9 ± 0.2* |
| Failure Mode | 100% pull-out | 100% eyelet failure |

*Significant difference between the two groups

In the foregoing description of preferred embodiments of the present disclosure, various features are grouped together in a single embodiment to streamline the disclosure. This method of disclosure is not to be interpreted as reflecting an intention that the claimed embodiments of the disclosure require more features than are expressly recited in each claim. Rather, as the following claims reflect, inventive subject matter lies in less than all features of a single disclosed embodiment. Thus, the following claims are hereby incorporated into the foregoing description, with each claim standing on its own as a separate embodiment.

What is claimed is:

1. A suture anchor apparatus comprising: an anchoring member made from a metal-based material comprising magnesium and comprising a generally elongated body having a proximal end and a distal end, wherein an outer surface of the anchoring member defines a threading that winds around the body in a plurality of turns disposed along a longitudinal axis of the body; wherein the threading has a depth of about 1 mm and a pitch of about 3 mm, wherein the threading tapers from a base to an outer most edge, the threading having adjacent bases that are spaced-apart by 1-2 mm; an eyelet disposed near the distal end and penetrating transversely through the body; and opposed flats within longitudinal slots extending along opposite outer sides of the elongated body and intersecting with the eyelet to provide clearance for sutures extending alongside the elongated body.

2. The suture anchor apparatus of claim 1 wherein the metal-based material comprises a magnesium alloy.

3. The suture anchor apparatus of claim 2 wherein the metal-based material is biodegradable.

4. The suture anchor apparatus of claim 2 wherein the metal-based material is biodegradable and causes no interference with the operation of an MRI device.

5. The suture anchor apparatus of claim 2 wherein the metal-based material has a rate of biodegradability that is uniform over time.

6. The suture anchor apparatus of claim 2 wherein the metal-based material has a rate of biodegradability that has been customized by the inclusion of alloying materials selected from the group consisting of calcium, zinc and manganese, and/or by surface treatments.

7. The suture anchor apparatus of claim 6 wherein the rate of biodegradability corresponds to an anticipated healing time.

8. The suture anchor apparatus of claim 6 wherein the rate of biodegradability corresponds to an anticipated healing time such that the anchoring member will only completely degrade after such anticipated healing time has passed.

9. The suture anchor apparatus of claim 2 wherein the metal-based material promotes bone growth, or has high osteoinductivity or high osteointegration.

10. The suture anchor apparatus of claim 2 wherein the metal-based material has a rate of biodegradability that has been customized by the inclusion of alloying materials and/or by surface treatments.

11. The suture anchor apparatus of claim 1 wherein the metal-based material comprises an AZ31 magnesium alloy.

12. The suture anchor apparatus of claim 1 wherein the metal-based material causes no interference with the operation of an MRI device.

13. The suture anchor apparatus of claim 1 wherein the metal-based material is biodegradable.

14. The suture anchor apparatus of claim 1 wherein the metal-based material is biodegradable and causes no interference with the operation of an MRI device.

15. The suture anchor apparatus of claim 1 wherein the metal-based material has a rate of biodegradability that is uniform over time.

16. The suture anchor apparatus of claim 1 wherein the metal-based material has a rate of biodegradability that has been customized by the inclusion of alloying materials selected from the group consisting of calcium, zinc and manganese, and/or by surface treatments.

17. The suture anchor apparatus of claim 1 wherein the metal-based material promotes bone growth, or has high osteoinductivity or high osteointegration.

18. The suture anchor apparatus of claim 16 wherein the rate of biodegradability corresponds to an anticipated healing time.

19. The suture anchor apparatus of claim 16 wherein the rate of biodegradability corresponds to an anticipated healing time such that the anchoring member will only completely degrade after such anticipated healing time has passed.

* * * * *